United States Patent [19]

Mulvey et al.

[11] Patent Number: 4,565,692
[45] Date of Patent: Jan. 21, 1986

[54] EXTRUDABLE DENTIFRICE

[75] Inventors: Patricia S. Mulvey, Manalapan; Jordan B. Barth, East Brunswick; Linda J. Vellekoop, Neshanic, all of N.J.

[73] Assignee: Colgate-Palmolive Company, New York, N.Y.

[21] Appl. No.: 564,968

[22] Filed: Dec. 23, 1983

[51] Int. Cl.$^4$ ................................................ A61K 7/16
[52] U.S. Cl. ......................................... 424/57; 424/49
[58] Field of Search ..................... 222/192; 424/49-58

[56] References Cited

U.S. PATENT DOCUMENTS

| 3,828,977 | 8/1974 | Borchert | 222/95 |
|---|---|---|---|
| 3,838,796 | 10/1974 | Cohen | 222/105 |
| 3,932,606 | 1/1976 | Barth et al. | 424/52 |
| 3,939,261 | 2/1976 | Barth | 424/52 X |
| 4,029,760 | 6/1977 | De Roeck et al. | 424/48 |
| 4,171,757 | 10/1979 | Diamond | 222/389 |
| 4,353,890 | 10/1982 | Scott | 424/49 |
| 4,444,747 | 4/1984 | Hayes et al. | 424/52 |
| 4,473,988 | 10/1984 | Scott | 424/49 |
| 4,482,536 | 11/1984 | Hayes et al. | 424/52 |

FOREIGN PATENT DOCUMENTS

| 115711 | 9/1981 | Japan . |
| 2070695 | 9/1981 | United Kingdom . |

*Primary Examiner*—Shep K. Rose
*Attorney, Agent, or Firm*—Robert L. Stone; Herbert S. Sylvester; Murray M. Grill

[57] ABSTRACT

A dentifrice of desirable rheological properties suitable for extrusion from a mechanically operated or presssure differential dentifrice dispenser, which dentifrice comprises a polishing agent including dicalcium phosphate or a siliceous polishing material and a gelling agent containing iota-carrageenan or a mixture of iota-carrageenan with a cellulosic gelling agent such as sodium carboxymethyl cellulose.

8 Claims, No Drawings

EXTRUDABLE DENTIFRICE

This invention relates to an extrudable dentrifrice. In particular, it relates to a dentifrice having desirable rheological properties such as being a readily extrudable dentifrice when packaged in a mechanically operated or pressure differential dentifrice dispenser.

A dentifrice is generally recognizable by its creamy or gel consistency and may commonly be called a dental cream, a toothpaste or, in some cases, a clear gel or opacified gel toothpaste. Indeed, it can be characterized as a semi-solid, for instance, being essentially solid when standing on the bristles of a toothbrush and essentially liquid such as during manufacture with agitation or when subject to pressure to extrude the dentifrice from its container. Such liquification is greatest when a pressure differential dispenser is employed due to its typically narrow orifice.

The creamy or gel consistency of dentrifrices is imparted by a gelling or binding agent, sometimes supplemented with a non-gelling thickener. In the past, gelling agents have been selected primarily to provide case of dispersion of the dentifrice in the oral cavity. Many gelling agents such as cellulosic materials, seaweed derivatives, gums and clays meet this criteria. However, some gelling agents while generally desirable for dentifrices packaged in flexible tubes, do cause rheological disadvantages when the dentifrices are packaged in a mechanically operated or pressure differential dispensers.

Dentifrices containing conventional polishing agents such as dicalcium phosphate including each of the anhydrous and dihydrate forms and mixtures thereof and conventional gelling agents such as sodium carboxymethyl cellulose or hydroxyethyl cellulose, although often recommended for and used with such dentifrices, have tended to thicken with the passage of time. A similar problem occurs when a siliceous polishing agent such as silica xerogel, hydrous silica, precipitated silica or amorphous silica containing combined alumina; that is essentially an aluminosilicate such as sodium aluminosilicate, is employed. Kappa carrageenan gelling agent, which has also been recommended, tends to cause such dentifrices to become thin upon being sheared when passing through a container orifice.

Dentifrices which thicken may become increasingly difficult for a consumer to extrude from a dentifrice tube over a period of time. In other words, the consumer may have to increase pressure on a dentifrice tube containing such a dentrifrice during the period of use in order to soften or liquify the semi-solid dentifrice mass to extrude it. This has not been a major problem in the past since formulations can be adjusted to use less gelling agent to strike a balance at not being too soft at the start of use and too thick at the end and in any event consumers have readily adjusted to applying the amount of pressure necessary to extrude the desired amount of dentifrice onto bristles of a toothbrush.

Dentifrices which are thin upon extrusion from a tube have also been tolerated during use if they set to more solid form on toothbrush bristles within a few seconds. Thus, the type of gelling agent could be widely varied for dentifrices packaged in tubes. Indeed, the Copenhagen Pectin Factory, Ltd. of Little Skensved, Denmark, a subsidiary of Hercules, Inc., of Wilmington, Del., U.S.A. has proposed its product Genuvisco Type 0819, an iota-carrageenan (i-carrageenan), as a possible thickener for toothpaste. I-carrageenan available from Marine Colloids Division of FMC Corp. of Springfield, N.J., as Viscarin TP-5 has also been proposed for possible toothpaste use with toothpaste containing dicalcium phosphate or silica. Indeed, i-carrageenan has been disclosed as a thickener component together with k-carrageenan and alkali metal alginate for a dentifrice containing galactan galactose in Japanese Patent Publication 56 115711, published Sept. 11, 1981, of Lion Dentifrice Ltd. Xanthan is another type of gelling agent which can be used to make a dicalcium phosphate or siliceous polishing agent less prone to thicken.

When a dentifrice dispenser which operates mechanically or by pressure differential is employed, conventional techniques of reducing thickening of dentifrice containing dicalcium phosphate or siliceous polishing agent are not fully satisfactory. Likewise, since the tendency to liquify is increased during shearing and extrusion, particularly from pressure differential dispensers, gelling agents which produce thin dentrifrices are also not fully satisfactory as they tend to be too slow to reset to solid form after extrusion. When conventional gelling agents such as sodium carboxymethyl cellulose or hydroxyethyl cellulose are employed, the dentifrice becomes too thick to extrude through the orifice of the dispenser or extrude only with substantial difficulty. In fact, if dentifrice containing such gelling agent can be extruded, it then becomes unduly thin upon shearing. With k-carrageenan the dentifrice is too thin upon shearing. Reduced levels of such gelling agents tend to make the product too soft or liquid such that it does not stand up well upon bristles of toothbrush when extruded but rather becomes flat and sags. Alternative types of gelling agents such as xanthan tend to make the dentifrice soft and stringy.

Unexpectedly from amongst alternative types of gelling agents, i-carrageenan provides excellent rheology for a dentifrice containing dicalcium phosphate or siliceous polishing agent which is to be extruded from a mechanical or pressure differential dispenser. This is the case when i-carrageenan is used as the sole gelling agent. Moreover, when i-carrageenan is used in mixture with cellulosic gelling agent additional desirable rheology characteristics of such gelling agents are obtained without undue thickening. It is noteworthy that xanthan has not been compatible with cellulosic gelling agents since it may contain cellulase.

It is an advantage of this invention that a dentifrice is provided which is readily extrudable from a mechanically operated or pressure differential dentifrice dispenser with desirable rheological properties.

It is an advantage of this invention that desirable dentifrice rheological properties associated with cellulosic gelling agent are retained while undue dentifrice thickening is avoided.

Other advantages will be apparent from consideration of the following specification.

In accordance with certain of its aspects, this invention relates to a dentifrice in a mechanically operated or pressure differential dispenser comprising about 20–80% by weight of an aqueous humectant vehicle, about 0.1–5% by weight of gelling agent and about 10–75% by weight of polishing agent, which dentifrice contains as polishing agent at least about 20% by weight of dicalcium phosphate based upon the weight of the dentifrice or at least about 10% by weight of a siliceous polishing agent, wherein said gelling agent is i-carrageenan in amount of about 0.1–2.5% by weight of the dentifrice or a mixture in amount of about 0.1–2.5% by weight of the dentifrice of i-carrageenan mixed with a cellulosic gelling agent in a weight ratio of i-carrageenan to cellulosic gelling agent of about 99:1 to about 1:3, and the total gelling agent is present in amount of up to about 5% by weight.

In the dentifrice formulation the dental vehicle comprises a liquid phase proportioned with the gelling agent to form an extrudable creamy mass of desirable consistency. The liquid phase in the dentifrice will comprise chiefly water and humectant such as polyols including glycerine, sorbitol, maltitol, xylitol, low molecular weight polyethylene glycol (e.g. 400 or 600), propylene glycol or the like including suitable mixtures thereof. It is advantageous usually to use as the liquid phase water and a humectant such as glycerine, sorbitol or polyethylene glycol, typically in amounts of about 10–55% by weight of water and about 20–50% by weight of humectant in a dentifrice containing dicalcium phosphate as the main polishing agent. In a dentifrice containing a siliceous polishing agent about 3–50% by weight of water and about 20–70% by weight of humectant is usually used.

The dentifrice contains dicalcium phosphate or siliceous polishing agent including mixture thereof, in amounts of about 10–75% by weight. Dicalcium phosphate, when present, comprises at least about 20% by weight of the dentifrice. Siliceous polishing agent, when present, comprises at least about 10% by weight of the dentifrice, typically about 10–30% by weight. Dicalcium phosphate may be used in its dihydrated or anhydrous forms or as mixtures thereof in any desired ratio. Most typically dicalcium phosphate is employed, generally as the dihydrate. Dicalcium phosphate is typically the sole polishing agent, but if desired minor amounts (e.g. up to about 20% by weight of the dental cream and less than the amount of dicalcium phosphate) of other dentally acceptable water-insoluble polishing agents which do not substantially interfere with the ability of the composition of the invention to promote oral hygiene may be present. Siliceous polishing agents, besides being a main polishing agent, may also be an additional polishing agent to dicalcium phosphate. Other typical additional polishing agents include hydrated alumina, anhydrous alumina and calcium carbonate. A minor amount of hydrated alumina (e.g. about 1%) also inhibits or even eliminates the tendency of some dental cream to separate or "bleed" in their tubes.

Siliceous polishing agent includes an amorphous silica containing combined alumina which can be considered to be an alkali metal aluminosilicate having a refractive index of from 1.44 to 1.47 and containing at least 70% silica, up to 10% alumina, such as about 0.1–10% e.g. about 0.1–3%, preferably up to about 20% of moisture, such as about 0.5–10%; and up to about 10% of alkali metal oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of alkali metal oxide is from 5% to 10%. Generally, the polishing agent has a loose bulk density of up to 0.2 g/cc, such as from 0.07 to 0.12 g/cc.

Another suitable type of polishing agent is porous amorphous silicic anhydride having an average particle size preferably below 20 microns and above 1 micron, a surface area of at least 200 $m^2/g$, preferably at least 300 $m^2/g$, and a bulk density of at least 0.15 $g/cm^3$, preferably at least 0.30 $g/cm^3$, such as a dehydrated silica hydrogel (i.e. a xerogel), preferably of the well known regular density or intermediate density type. Examples of such amorphous silicic anhydride polishing agents are "Syloid 63", "Syloid 72", and "Syloid 74" (SYLOID is a trade mark) which are described in "The Davison Family of Syloid Silicas" published by their manufacturer, Grace, Davison Chemical Company, "Santocel 100" of Monsanto (SANTOCEL is a trade mark), is also a suitable dental abrasive. "Syloid 72" has an average particle size of about 4 microns, a surface area of about 340 $m^2/g$ bulk density of about 1.77 $g/cm^3$. For "Syloid 63" the corresponding figures are about 9 microns, about 675 $m^2/g$ and about 0.4 $g/cm^3$. A grade of "Santocel 100" has a surface area of about 239 $m^2/g$ and a bulk density of about 0.24 $g/cm^3$. These amorphous silicic anhydrides may be used singly or in mixtures.

Hydrous silica which may be used as polishing agent is particularly described in British Published Patent Application 2 038 303A of Grace G.m.b.H. The hydrous gel is generally described as having an average particle size of 1 to 30 microns and:

(a) a surface area of 1 to 600 $m^2/g$.
 (b) a pore volume of 0.05 to 0.5 $cm^3/g$,
 (c) a product of surface area (in $m^2/g$) × pore volume (in $cm^3g$) less than or equal to 240,
 (d) a calculated pore diameter of 1.5 to 2.5 nm, and
 (e) a water content of less than 25% by weight.

Polishing agent in the form of synthetic hydrated precipitated silica is not a silica gel, xerogel or aerogel, but is obtained as a finely divided precipitate, such as from a solution of alkali metal silicate and acid. The variables of concentration, pH and temperature are chosen to prevent the formation of a continuous gelatinous mass and to promote the precipitation of silica in a finely divided form which can be readily filtered and washed.

The gelling agent of the present invention is present in the dentifice amount of about 0.1–5% by weight. It may be entirely i-carrageenan in amount of about 0.1–2.5% by weight or a mixture in amount of about 0.1–2.5% by weight of i-carrageenan mixed with a cellulosic gelling agent, wherein the weight ratio of said i-carrageenan to said cellulosic gelling agent is from 99:1 to about 1:3, preferably from about 2:1 to about 1:3 and particularly about 2:1 to about 3:2 or about 3:2 to about 1:1, and the total gelling agent mixture is present in an amount up to about 5% by weight, preferably about 0.2–3%. The yield point value of the dentifrice is desirably in the range of 2000–5000 dynes/$cm^2$, preferably about 2000–4000 dynes/$cm^2$, from the time the dentifrice sets after preparation for at least about three months when maintained at room temperature (measured on Haake Rotovisco Viscometer using a profiled SVIIP cup).

As mentioned above, iota carrageenan is commercially available as Genuvisco type 0819 and Viscarin TP-5 and has been recommended for use in a toothpaste. Such use in a toothpaste was described in Japanese Patent Publication 56 115711 of Lion Dentifrice Ltd., wherein i-carrageenan is mentioned as a possible component of a gelling system together with k-carrageenan and alkali metal alginate. In U.S. Pat. No. 4,353,890 to Scott, i-carrageenan is disclosed as an alternative to k-carrageenan as a toothpaste gelling agent wherein the toothpaste is subjected to microwave radiation to reduce the tendency of carrageenan in general to become thin during manufacture. The carrageenan may be sole gelling agent or mixed with other gelling agents. In the present invention, dentifrice containing i-carrageenan to be packaged in a mechanically operated or pressure differential dispenser does not require microwave radiation.

The prior art generally discussed above does not indicate that gelling systems based on i-carrageenan can provide dentifrices containing dicalcium phosphate or siliceous polishing agent with the rheology necessary for long-term extrusion from a mechanically operated or pressure differential dispenser.

It is noteworthy that U.S. Pat. No. 4,029,760 to de Roeck et al discloses an oral composition in which i-carrageenin is set forth as an antigingivitis agent alternative to other carrageenins. Carrageenins are highly depolymerized derivatives of carrageenans. Carrageenans do not appear to provide an antigingivitis effect.

Dentifrices are commonly manufactured by a cold process, e.g. at about 25° C., or by a hot process, e.g. at about 60° C. I-carrageenan can be used in either cold process or hot process techniques. K-carrageenan can only be used with hot processing.

Physical properties of Genuvisco type 0819 i-carrageenan are indicated below;
1. Viscosity of 0.30% solution of GENUVISO type 0819 in lean solvent prepared using a hot process (60° C.):
   Viscosity=690±80 cP measured on Brookefield Viscometer LVT at 25° C.
   Viscosity=110±17 cP at 32 rpm.
   Viscosity=70±11 cP at 64 rpm.
   Viscosity=45±7 cP at 128 rpm.
   Measured on HAAKE Rotovisco RV3 at 25° C.
2. Viscosity of 0.30% solution of GENUVISCO type 0819 in lean solvent prepared using a cold process (25° C.):
   Viscosity=450±60 cP measured on Brookfield Viscometer LVT at 25° C.
   Viscosity=86±13 cP agt 32 rpm.
   Viscosity=55±8 cP at 64 rpm.
   Viscosity=37±6 cP at 128 rpm.
   Measured on HAAKE Rotovisco RV3 at 25° C.
3. Particle size: Less than 1% gum on 0.075 mm test sieve (DIN 80, 200 US mesh).
4. Moisture content: Less than 12%.
5. pH: 8.5±1.5 in 0.5% solution in distilled water at 25° C.
6. Color; White to cream.

Viscarin TP-5 i-carrageenan has the following physical properties:
Color; light tan to tan
Particle size: more than 95.0% through a U.S. Standard Sieve, 250 nm (Series #60).
Moisture: maximum 12.0% (Cenco Moisture Balance).
pH: 7.0 to 9.5, 1.5% solution, 30° C. (86° F.).

When i-carrageenan is mixed with a cellulosic gelling agent in a dentifrice containing dicalcium phosphate or siliceous polishing agent, thickening does not occur to interfere with extrusion from a mechanically operated or pressure differential dispenser and other rheological properties such as consistency and stand-up to touch are improved. Typical desirable cellulosic gelling agents include alkali metal carboxymethyl cellulose, methyl cellulose, hydroxyethyl cellulose and hydroxypropyl cellulose. Sodium carboxymethyl cellulose is preferred. When the mixed gel system is present in amount up to about 5% by weight of the dentifrice, about 0.1-2.5% of the dentifrice is i-carrageenan and the weight ratio of i-carrageenan to cellulosic gelling agent is from about 99:1 to about 1:3, preferably about 2:1 to about 1:3, such as about 3:2 to about 2:1 or about 1:1. Thus, a typical dentifrice can contain about 0.9-1.2% total gelling agent including about 0.3-0.9% of each of i-carrageenan and cellulosic gelling agent, the weight ratio between the two being from about 3:2 to about 2:1 or about 2:1 to about 1:2.

It is noteworthy that grades of sodium carboxymethyl cellulose which may be used include the following:

TABLE 1

| SUPPLIER | CMC GRADE | VISCOSITY (CP) |
|---|---|---|
| Hercules | 7MXF | 300–500 |
| Hercules | 7MFD | 300–500 |
| Hercules | 9M31F | 900–1200 |
| Hercules | 9M31XF | 900–1200 |
| Hercules | 12M31XF | 900–1200 |
| Hercules | 7MF | 300–500 |
| Hercules | 12M31PD | 900–1200 |
| Hercules | 7M8SXF | 200–800 |
| Wolff Walsrode | Walocel CRT 1000 PA 09 | 700–1200 |
| Nyma | Nymcel ZMF.33* | 50–80 |
| Enka | Akucell AC 1642* | 80–120 |
| Enka | Akucell AC 1632* | 60–120 |
| Cros | Cellogen HP-SA | 700–900 |
| Uddeholm | Cekol MVEP | 500–800 |
| Hoechst | Tylose CB 200** | 120–260 |

*1% solution (Brookfield; 25° C.)
**Hoeppler Viscometer (2%; 20° C.)

Further, grades of hydroxyethyl cellulose which may be used include the following:

TABLE 2

| SUPPLIER | HEC GRADE | VISCOSITY (CP) |
|---|---|---|
| Hercules | Natrosol 250 M and MR | 4500–6500 |
| Hercules | Natrosol 250 HR* and 250 H* | 1500–2500 |
| Hercules | Natrosol 250 HHR* and 250 HH | 3400–5000 |
| B.P. Chemicals | Cellobond 5000 A | 4200–5600 |
| B.P. Chemicals | Cellobond 7000 A | 6000–7000 |
| Hoechst | Tylose H 4000 P** | 3000–5000 |
| Hoechst | Tylose H 10000 P** | 7000–12000 |

*1% solution (Brookfield; 25° C.)
**Hoeppler Viscometer (2%; 20° C.)

The i-carrageenan and cellulosic gelling agent may be mechanically mixed together prior to mixing with the liquid phase of the dental cream vehicle or may be mixed separately with the liquid phase, with hot processing (typically about 60° C.) or cold processing (typically about 25° C.) techniques.

Synthetic finely divided silicas such as those sold as the "Cab-O-Sil M-5", "Syloid 244", "Syloid 266", "Aerosil D200" and mixtures thereof, may also be employed, e.g. in amounts of from 0.5% to 20%, to promote thickening of the dentifrice, particularly when the dentifrice contains siliceous polishing agent. Amounts in the range of about 5–10% by weight are preferred.

The dentifrice is packaged in a container from which it can be readily extruded such as a pressure differential or mechanically operated dental cream dispenser. The rheological properties are highly desirable when a mechanically operated dispensing container of the type described in British Patent Application 2,070,695A, published Sept. 9, 1981, is employed. This dispensing container comprises a dispensing mouthpiece, a tension member, a central rod, a piston and operating hand control. The disclosure of this published application is incorporated herein by reference. Pressure differential dispensing container may be of the aerosol or vacuum type.

The advantages of the present invention are particularly evident when a pressure differential dispenser is employed since such dispensers have quite narrow orifices, typically about 50 mm² or less, which do not permit extrusion of thick compositions and which produce high shear effects on extruded products.

Suitable pressure differential dispensers include those comprising a collapsible product-containing bag being disposed within a rigid container which contains a propellant fluid. In such dispensing containers, operation of the valve permits release of the product only, the propellant fluid being separated from the product by the fluid impermeable bag. Dispensers of this type are described in U.S. Pat. Nos. 3,828,977 and 3,838,796. These are the so-called Sepro dispensers. So-called Exxel containers also utilize pressure.

Still another type dispenser is the barrier piston container described in U.S. Pat. No. 4,171,757. Such container includes a valve, a product-containing compartment and an essentially fluid-tight barrier piston which separates the propellant fluid from the contained product (The so-called Diamond container).

Filling is effected by conventional techniques. For instance, when a mechanically operated dispenser of the type described in Published British Patent Application 2,070,695A is used a predetermined amount of the dentifrice is extruded through a nozzle to fill the dispenser which is open at its bottom and which contains a central rod. A piston having a diameter corresponding to the inner diameter of the dispenser and a central hole to permit insertion of the central rod therein is slid into place. The dispenser is then sealed with a bottom disc.

The dentifrice may contain a compound which provides at least about 100 ppm, of fluoride, typically about 100–10000 ppm, typically about 750–2000 ppm. Compounds which provide fluorine include sodium fluoride, stannous fluoride, potassium fluoride, potassium stannous fluoride, sodium hexafluorostannate, stannous chlorofluoride, sodium monofluorophosphate and amine fluorides including mixtures thereof. Most typically in accordance with the present invention sodium fluoride, sodium monofluorophosphate or a mixture of sodium monofluorophosphate and sodium fluoride may be employed.

The dentifrice may preferably contain sodium monofluorophosphate or a mixture of sodium monofluorophosphate and sodium fluoride in amount to provide about 100–10000 ppm of fluorine, e.g. about 750–2000 ppm, and particularly about 1400–2000 ppm, such as about 1400–1670 ppm. A binary fluoride system of sodium monofluorophosphate and sodium fluoride is desirably used in which about 30–40% of the fluorine (e.g., about 30–35%) is provided by sodium fluoride.

Sodium monofluorophosphate, $Na_2PO_3F$, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more than 1.5%, preferably not more than 1.2% of free sodium fluoride; and a sodium monofluorophosphate content of at least 12%; preferably at least 12.1% all calculated as fluoride.

As indicated above, sodium fluoride in the binary mixture is a separate fluorine-containining component from sodium monofluorophosphate. About 225–800 ppm of fluorine is preferably provided to the dental cream by sodium fluoride.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble compounds usually, and may be anionic, nonionic, or cationic in structure. It is usually preferred to use the water-soluble non-soap or synthetic organic detergents. Suitable detersive materials are known and include, for example, the water-soluble salts of higher fatty acid monoglyceride monosulphate detergent (e.g., sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2-dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarconsine, alanine, 3-aminopropanoic acid and valine having about 12 to 16 carbon in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sarcosides, ammonium and ethanolamine N-lauroyl glycide and alanine. For convenience herein, reference to "amino carboxylic acid compound", "sarcoside", and the like refers to such compounds have a free carboxylic group of the water-soluble carboxylate salts.

Such materials are utilized in pure or substantially pure form. They should be as free as practicable from soap or similar higher fatty acid material which tends to reduce the activity of these compounds. In usual practice, the amount of such higher fatty acid materials is less that 15% by weight of the amide and insufficient to substantially adversely affect it, and preferably less than about 10% of said amide material.

Various other materials may be incorporated in the dentifrices of this invention. Examples thereof are colouring or whitening agents, preservatives, such as methyl p-hydroxybenzoate or sodium benzoate, stabilisers, tetrasodium pyrophosphate, silicones, chlorophyll compounds and ammoniated materials such as urea, diammonium phosphate and mixtures thereof. These adjuvants are incorporated in the instant compositions in amount which do not substantially adversely affect the desired properties and characteristics and are suitably selected and used in conventional amounts.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-(2,4-dichlorobenzyl)biguanide;
p-chlorophenyl biguanide;
4-chlorobenz hydryl biguanide;
4-chlorobenz hydrylguanylurea;
N-3-lauroxypropyl-$N^5$-p-chlorobenzylbiguanide;
1,6-di-p-chlorophenylbiguanihexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring, constituents include the flavouring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable flavour and sweetening agent may together comprise from about 0.01 to 5% or more of the composition.

The dentifrices should have a pH practicable for use. A pH range of 5 to 9 is particularly desirable. The reference to the pH is meant to be the pH determination directly on the dentifrice. If desired, materials such as benzoic, or citric acid may be added to adjust the pH to, say 5.5 to 6.5.

The following examples are further illustrative of the nature of the present invention, but it is to be understood that the invention is not limited thereto. All amounts of the various ingredients are by weight unless otherwise specified.

EXAMPLE 1

The following dentifrices are prepared by conventional hot process at 60° C.

| | PARTS | | |
|---|---|---|---|
| | A | B | C |
| Glycerine | 22.00 | 22.00 | 22.00 |
| Sodium carboxymethyl cellulose (7-MF) | 1.00 | — | 0.30 |
| I-Carrageenan (Genuvisco 0819) | — | 0.90 | 0.60 |
| Sodium saccharin | 0.20 | 0.20 | 0.20 |
| Sodium benzoate | 0.50 | 0.50 | 0.50 |
| Sodium monofluorophosphate | 0.76 | 0.76 | 0.76 |
| Tetrasodium pyrophosphate | 0.25 | 0.25 | 0.25 |
| Dicalcium phosphate dihydrate | 48.76 | 48.76 | 48.76 |
| Sodium lauryl sulphate | 1.20 | 1.20 | 1.20 |
| Flavour | 0.84 | 0.84 | 0.84 |
| Deionized water | 24.49 | 24.59 | 24.59 |

Each dentifrice is filled into the mechanically operated dispenser described in British Patent Publication No. 2,070,695 A and the yield point values determined in a Haake Rotovisco Viscometer using a profiled SVIIP cup initially (2 days following preparation), and after ageing for periods at room temperature. The results are as follows:

| | Yield Point Value (Dynes/cm$^2$) | | | |
|---|---|---|---|---|
| Dentifrices | Initial | 2 weeks | 1 month | 3 months |
| A | 4380 | 5030 | 5760 | 7080 |
| B | 3190 | 3370 | 3610 | |
| C | 3190 | 2420 | 2610 | 2970 |

Dentifrice A is initially somewhat thick and thickens considerably more during ageing so that it is difficult to satisfactorily extrude from the mechanically operated dispenser.

Dentifrices B and C have initially excellent rheology characteristics and extrude well from the mechanically operated dispenser after ageing. Indeed, Dentifrice C does not even measurably thicken during the ageing period.

When each of Dentifrices A, B and C are filled into the pressure differential dispenser described in U.S. Pat. No. 4,171,757, Dentifrice A becomes too thick to extrude through the orifice of the dispenser, while Dentifrices B and C retain excellent rheology and extrude well.

Similar results occur when the dentifrices are made by conventional cold process at room temperature.

A modification of Dentifrice C in which flavour is increased to 0.89 parts and deionized water reduced to 24.54 also retains excellent rheology and extrusion characteristics from the mechanically operated and pressure differential dispensers.

Similar results are obtained when hydroxyethyl cellulose replaces sodium carboxymethyl cellulose.

EXAMPLE 2

The following dentifrices are prepared by conventional hot process at 60° C. and by conventional cold process at room temperature and filled into each of the mechanically operated dispenser of British Patent Publication 2,070,695 A and the pressure differential dispenser of U.S. Pat. No. 4,171,757.

| | PARTS | |
|---|---|---|
| | D | E |
| Glycerine | 22.00 | 22.00 |
| Sodium carboxymethyl cellulose (7 MF) | 0.36 | 0.45 |
| I-Carrageenan (Genuvisco 0819) | 0.54 | 0.45 |
| Sodium saccharin | 0.20 | 0.20 |
| Sodium benzoate | 0.50 | 0.50 |
| Sodium monofluorophosphate | 0.76 | 0.76 |
| Tetrasodium pyrophosphate | 0.25 | 0.25 |
| Dicalcium phosphate dihydrate | 48.76 | 48.76 |
| Sodium lauryl sulphate | 1.20 | 1.20 |
| Flavour | 0.84 | 0.84 |
| Deionized water | 24.59 | 24.59 |

The dentifrices have desirable rheology and extrusion characteristics initially and after storage.

EXAMPLE 3

The following dentifrices are prepared by conventional cold process at room temperature and filled into each of the mechanically operated dispenser described in British Patent Publication 2,070,695 A and the pressure differential dispenser described in U.S. Pat. No. 4,171,757.

|  | PARTS | |
| --- | --- | --- |
|  | F | G |
| Glycerine | 25.00 | 25.00 |
| Sodium carboxymethyl cellulose (7 MF) | 1.50 | 0.75 |
| I-Carrageenan (Genuvisco 0819) | — | 0.75 |
| Sodium saccharin | 0.20 | 0.20 |
| Sodium benzoate | 0.50 | 0.50 |
| Titanium dioxide | 0.40 | 0.40 |
| Sodium fluoride | 0.22 | 0.22 |
| Amorphous silica containing about 1% combined alumina (Zeo 49-Huber) | 22.00 | 22.00 |
| Silica thickener (Syloid 244) | 5.00 | 5.00 |
| Sodium lauryl sulphate | 1.50 | 1.50 |
| Flavour | 1.00 | 1.00 |
| Deionised water | 42.68 | 42.68 |

Dentifrice F thickens and extrudes poorly from the dispenser, Dentifrice G has desirable rheology and extrudes well initially and after storage.

It will be apparent to those skilled in the art that further modifications of the examples illustrative of the invention, may be made thereto.

We claim:

1. A dentifrice suitable for use in a mechanically operated or pressure differential dispenser comprising about 20-80% by weight of an aqueous humectant vehicle, about 0.1-5% by weight of gelling agent and about 10-75% by weight of polishing agent, which dentifrice contains as polishing agent at least about 20% by weight of dicalcium phosphate based upon the weight of the dentifrice or at least about 10% by weight of a siliceous polishing agent, wherein said gelling agent is i-carrageenan in amount of about 0.1-2.0% by weight of the dentifrice or a mixture of in amount of about 0.1-2.5% by weight of the dentifrice of i-carrageenan mixed with a cellulosic gelling agent in a weight ratio of i-carrageenan to cellulosic gelling agent of about 99:1 to about 1:3 and the total gelling agent is present in amount of up to about 5% by weight.

2. The dentifrice claimed in claim 1 wherein i-carrageenan is the only gelling agent present.

3. The dentifrice claimed in claim 2 wherein said polishing agent is dicalcium phosphate dihydrate.

4. The dentifrice claimed in claim 1 wherein said gelling agent is a mixture of i-carrageenan and cellulosic gelling agent in a weight ratio of i-carrageenan to cellulosic gelling agent of from about 2:1 to about 1:3.

5. The dentifrice claimed in claim 4 wherein said weight ratio is from about 2:1 to about 3:2 and said polishing agent is dicalcium phosphate dihydrate.

6. The dentifrice claimed in claim 5 wherein said cellulosic gelling agent is sodium carboxymethyl cellulose.

7. The dentifrice claimed in claim 4 wherein said weight ratio is from about 3:2 to about 1:2 and said polishing agent is dicalcium phosphate dihydrate.

8. The dentifrice claimed in claim 7 wherein said cellulosic gelling agent is sodium carboxymethyl cellulose.

* * * * *